United States Patent [19]

Sanders

[11] 4,162,303

[45] Jul. 24, 1979

[54] POTENCY AND ATOXICITY TEST FOR MODIFIED NEUROTOXIN

[76] Inventor: Murray J. Sanders, 3009 Spanish Trail Rd., Delray Beach, Fla. 33444

[21] Appl. No.: 807,654

[22] Filed: Jun. 17, 1977

[51] Int. Cl.$^2$ .................... A61K 29/00; A61K 35/58; C12K 9/00

[52] U.S. Cl. .......................................... 424/9; 424/89; 424/93; 424/98; 435/235; 435/236; 435/237; 435/240; 435/241

[58] Field of Search ................... 424/9, 12, 89, 93, 98; 195/1.1, 1.2, 1.3, 1.7, 1.8; 23/230 B

[56] References Cited

U.S. PATENT DOCUMENTS 3,888,977  6/1975  Sanders .............................. 424/12 X

OTHER PUBLICATIONS

Lennette, Diag. Proc. for Viral & Rickettsial Dis. Am. Pub. Health Asso., 3rd Ed. 1964, pp. 112-119.
Frankel-Conrat (Ed) Comprehensive Virol., vol. 2, Cpt. 4, 1974, pp. 171-173, 176, 177, 187-189.
Andrewes, Viruses of Vertebrates, Bailliere, Tindall & Cassell Pub., London, 2nd Ed., 1967, pp. 74-75.
Speir, PSEBM, vol. 114, 1963, pp. 168-171.
DiMari, Biochim et Biophys. Acta, vol. 393, 1975, pp. 320-334.
Wyler, Chem. Abs., vol. 82, 1975, Ab. No. 165292c.
Miller, Biochim et Biophys. Acta, vol. 496, Jan. 24, 1977, pp. 192-196.

*Primary Examiner*—Anna P. Fagelson
*Attorney, Agent, or Firm*—Murray & Whisenhunt

[57] ABSTRACT

A method for proving the potency and atoxicity of modified neurotoxin is provided. A thin sheet of viable cells is provided on a growth substrate. Viability of the sheet of cells is defined as exhibiting an uninhibited growth potential of at least $10^6$ Plaque Forming Units of Semliki Forest virus. The sheet of cells is treated with the test modified neurotoxin and then inoculated with the Semliki Forest virus. The reduction in the number of plaques of Semliki Forest virus in the culture indicates the potency of the modified neurotoxin, since the modified neurotoxin interferes with plaque formation by the Semliki Forest virus in proportion to its potency. Atoxicity of the modified neurotoxin is demonstrated by lack of cell destruction.

16 Claims, No Drawings

POTENCY AND ATOXICITY TEST FOR MODIFIED NEUROTOXIN

The present invention relates to methods for proving the potency and atoxicity of modified neurotoxins. More particularly, the invention relates to such methods wherein the accuracies of potency and atoxicity determinations are increased, as opposed to methods heretofore available in the art. The invention, therefore, has particular relevancy in the manufacture of modified neurotoxin drugs for the treatment of degenerative neurological diseases, and especially such intractible diseases such as amyotropiclateral sclerosis.

BACKGROUND OF THE INVENTION

U.S. Pat. No. 3,888,977, issued on June 10, 1975, to Murray J. Sanders, discloses a method and composition for the treatment of degenerative neurological diseases of the nervous system which, among others, may involve the function of motor nerve cells from their origin to the neuromuscular junction, as well as elements of the central nervous system including axones, nerve myelin sheaths, etc. The present invention provides an improved method of performing the potency test and establishing atoxicity in the compositions of that patent. Hence, the entire disclosure of that patent is incorporated herein by reference and relied upon for the details of producing those compositions and for the method of treatment in connection therewith.

The Sanders patent notes that degenerative neurological diseases progress in a chronic manner to severe physical disability, such as paralysis, and even to death. While the cause of such neurological diseases is not always known, it is believed that the diseases are often caused by virus or proteins with potentially deleterious functions. It is further believed that these noxious moieties cause their degenerating functions by attaching to or involving nerve cell receptors. It is not clear whether nerve cell receptors are discrete anatomical structures of the nerve cell, or are theoretical biophysical concepts which describe on of the functions of the nerve cell. Irrespective, however, nerve cells act as if physical receptors exist in the nerve cell.

As also noted in the Sanders patent, certain neurotropic snake venoms have been shown to involve essentially all of the motor nerve cells, presumably at least in part through the nerve cell receptors, and the basic invention of the Sanders patent is that of blocking the nerve cell receptors by certain detoxified snake venom and thereby interfering with presumed invading pathogenic virus or protein moieties with potentially deleterious functions (or other moieties which may be indeed the cause of the neurological disease).

As can be easily appreciated, however, neurotropic snake venom, such as derived from the cobra and krait snakes, is extremely toxic and must be carefully detoxified before administrating to humans. On the other hand, the detoxification procedure can also be carried to a point where the modified snake venom is not only detoxified, but to where its neurotropic character is also destroyed. Thus, if the modified neurotoxin is carried through the detoxification procedure to that extent, it will not function in the manner intended by the Sanders patent.

The preferred detoxification procedure is that of mild oxygenation of a solution of the snake venom with the procedure being carried to the end point of toxicity but before deterioration of the neurotropic character commences. The usual method of following the detoxification process is by bioassay with laboratory animals. This test will determine lack of toxicity, but it does not give any indication of the potency of the detoxified snake venom.

The Sanders patent discloses a method of determining potency of a detoxified venom by an adaptation of the Semliki Forest virus test. In that test, a sheet of chick embryo fibroblastic tissue cells on glass is covered with a gelled nutrient preparation, such as Hank's solution with lactalbumin. As a control, Semliki Forest virus is inoculated on the chick cells and the number of resulting plaques show the titer of the virus. In the test, the chick cells are washed with a detoxified venom prior to inoculation with the control virus and if the detoxified venom has acceptable potency the cells will show few or no plaques of viral growth. If, however, a substantial number of plaques are observed, the detoxification procedure practiced with the venom has been too severe or carried beyond the end point and unacceptable denaturization of the venom has occurred, i.e., the potency of the detoxified venom has been unacceptably reduced. The Sanders patent requires that the cells washed in the detoxified venom always show at least a statistically significant inhibition of plaque formation by the virus, e.g., 30%, especially 50% inhibition of the plaques and preferably at least 70% to 75% inhibition of the plaques.

While that Semliki Forest virus test does produce the results stated in the Sanders patent, the accuracy of the potency test is not as great as desired. Additionally, that test gives no indication of toxicity/atoxicity and the bioassay by animal test must be performed for that purpose. It would, therefore, be of substantial benefit in the art if the Semliki Forest virus test could be improved to give greater accuracy of the potency of the modified neurotoxin and at the same time at least give some indication of toxicity/atoxicity. This would materially aid in finding that delicate end point during the detoxification procedure.

OBJECTS OF THE INVENTION

It is therefore an object of the invention to provide an improved method for determining the potency of modified neurotoxins. It is a further object of the invention to provide an indication of toxicity/atoxicity by use of a modified Semliki Forest virus test. It is a further object of the invention to provide an improved method for determining the potency and toxicity/atoxicity wherein the test may be easily conducted and is open to less subjective interpretation than the test disclosed in the Sanders patent. Other objects will be apparent from the following disclosure and claims.

BRIEF DESCRIPTION OF THE INVENTION

The present invention is based on two basic discoveries. The first discovery is that the accuracy of the Semliki Forest virus test may be substantially increased if care is taken to prepare a thin cell sheet of the cells with which the Semliki Forest virus test is conducted. For purposes of the present specification and claims, the term "thin sheet of cells" is defined as less than that number of cells where vitality of the cells ceases, since the Semliki Forest virus test must be carried out with a cell population which is substantially viable. For most cells, this will require less than 10 layers of cells and usually less than 5 layers. Preferably 3 layers or less are used and ideally only a monolayer is used.

The second discovery is that certain types of cells provide greater accuracy of the Semliki Forest virus test, particularly in comparison with the chick embryo fibroblastic cells disclosed in the Sanders patent. The cells which provide this improved accuracy can be defined as viable cells which exhibit growth potential of at least $10^6$ Plaque Forming Units (PFU) of Semliki Forest virus.

Thus, there is provided a method for determining the potency of modified neurotoxins, as defined in the Sanders patent, comprising providing on a growth substrate a thin sheet of viable cells which exhibit an uninhibited growth potential of at least $10^6$ Plaque Forming Units of Semliki Forest virus; treating the thin cell sheet with test modified neurotoxin; inoculating the treated cell sheet with Semliki Forest virus; and counting the number of viral plaques in the resulting culture.

The viral inhibition produced by the test modified neurotoxin is, preferably, compared with a control culture prepared in the same manner as the test culture above, but without treating with the modified neurotoxin. The potency of the modified neurotoxin is determined by the percent reduction in viral plaques produced by the use of the modified neurotoxin in the culture.

It is a further important feature of the invention that the atoxicity/toxicity of the test modified neurotoxin may be determined by examining the cells after treating with the modified neurotoxin. Any remaining toxins will destroy the viable cells and this destruction is quite apparent from an examination thereof, particularly a microscopic examination.

DETAILED DESCRIPTION OF THE INVENTION

For purposes of the present specification and claims, the term "modified neurotoxin" is used in the same sense as that of the Sanders patent, i.e., detoxified and neurotropically active modified snake venom neurotoxin. The terms "viable cells which exhibit uninhibited growth potential of at least $10^6$ Plaque Forming Units of Semliki Forest virus" mean that under the herein defined test conditions, these cells are capable of growing $10^6$ Plaque Forming Units (PFU) of the Semliki Forest virus. Thus, this is a characteristic of the cells and not a process requirement of the method of the invention. The acceptability of cells can be determined by growing the Semliki Forest virus on the test cells. If $10^6$ Plaque Forming Units are grown, the cells have the required potential. The particular cells are not critical so long as that potential is present. Generally, however, to meet this requirement, the cells must be harvested from an embryo, fetus or baby specimen of a fowl or animal. Kidney cells harvested from these sources are particularly sensitive to the Semliki Forest virus and constitute a preferred embodiment, particularly baby hamster kidney cells, since these cells are easily obtained and are most sensitive to the Semliki Forest virus.

It is important that the viable cells be prepared in a thin cell sheet in order that, in turn, the cell sheet is viable within the definition above for "viable cells." If the cell sheet is too thick, the vitality of the cells in the sheet (cell sheet) is not sufficient and the sensitivity of the test is substantially reduced. If proper cells have been selected, i.e., capable of $10^6$ PFU, then the acceptability of the particular number of layers of cells can be determined by uninhibited growth of the Semliki Forest virus on that number of layers and the $10^6$ PFU value should be substantially retained. Generally, however, less than 5, e.g. less than 3 layers of cells, will be used and particularly it is preferred that no more than 2 layers of cells be used. Ideally, only a monolayer of cells is used. The monolayer of cells may be obtained in known manners, such as separating the cells with trypsin and harvesting the cells as a monolayer. The details of this procedure are well known in the art and will not be repeated herein for the sake of conciseness.

As will be explained more fully hereinafter, it is preferred that during a portion of the test procedure the cells are uppermost in a spacial configuration, i.e., the culture is turned upside down. This embodiment necessitates either a solid substrate or a solid overlay of a fluid substrate. Aside from this physical requirement for this particular embodiment, the substrate is not critical and may be any of the conventional growth or maintenance substrates, many of which are known to the art and will not be repeated for the sake of conciseness.

In the practice of the method of the invention, the provided thin sheet of viable cells is treated with the test modified neurotoxin. While there is considerable latitude in the amount of the modified neurotoxin used in the method, it has been found that for most detoxified products, from 0.05 to 0.5 ml. per standard 50 ml. test culture bottle containing the thin sheet of cells is acceptable, since this will ensure that all of the cells are adequately contacted with the test modified neurotoxin. Of course, this volume will be adjusted downwardly or upwardly depending upon any concentration or dilution of the modified neurotoxin which may have previously taken place and upon the volume of the test culture bottle.

It is preferred that the cells be incubated after treatment with the test modified neurotoxin. This ensures vitality of the cells and provides a period of time to detect the effect, if any, of the test modified neurotoxin on the culture. The effect, if any, may be visually detected but cell microscopic examination is preferred since it will show the first signs of cell change induced by the modified neurotoxin. Usually 10 minutes to 8 hours is sufficient incubation time, but at least ½ hour is preferred and more preferably at least 1 hour to 36 hours. The toxicity/atoxicity can be determined during these time periods. If there is residual toxicity in the modified neurotoxin, cells will be destroyed during the incubation period. Destroyed cells are most apparent, especially from a microscopic examination, since the cell walls are disrupted and cell content and debris spill out. Incubation and observation of the cells treated with the modified neurotoxin for up to 36 hours will ensure that sufficient time has been allowed for any small amounts of residual toxicity to accomplish its deleterious effect. It will be appreciated that when substantial toxicity remains, large numbers of cells will be quickly destroyed and shorter incubation periods or no incubation period will be required. But as atoxicity is approached, longer incubation periods will ensure that any residual toxicity will be observed.

After the modified neurotoxin-treated cells have been examined and the lack of toxicity has been determined, the treated cells are inoculated with the Semliki Forest virus. While this virus may be obtained from many sources, it is preferred that the American Type Culture Collection Semliki Forest virus be used in this test procedure. Further, it is preferred that the virus be increased in virulence by passage through animals, particularly at least for 3 or more passages, and preferably at least 10, and ideally at least 15. The passage is accomplished in the normal manner of inoculation and harvesting, which method is well known to the art. Also, it is preferred that the Semliki Forest virus be adapted to grow on the particular cells used in the test. Here again, this adaptation is accomplished by passage through the cells, i.e. growing plaques on a sample of the cells and transferring the plaques to another cell sample for growth thereon, etc. Substantial adaptation can take place in one passage, although it is preferred that at least 2 or 3 passages of the virus be performed.

After inoculating with the Semliki Forest virus, the culture will normally be incubated to ensure that viral growth has commenced and cell change has occurred. Preferably, conditions are provided where rapid viral growth will take place unless interfered with in that growth by the modified neurotoxin. Incubation times of the inoculated cells will normally be between 8 hours and 72 hours, but often viral growth will be sufficient in at least 1 hour so that cell change can be detected microscopically.

The Semliki Forest virus inoculated cells may be overlaid with a solid inert growth or maintenance overlay. An overlay is preferred so that the culture may be inverted during at least part of the incubation period so that the cells are uppermost in the culture, e.g. in the tube or bottle or dish. The overlay ensures close contact between the virus, cells and substrate so that any possible effects of the virus on the cells can take place and be more easily observed. If an overlay is used, it may be placed on the inoculated cells either prior to or during incubation. Preferably, the inoculated cells are incubated for a short time, e.g. at least 1 or 2 hours, and then the overlay is put in place and the incubation is then continued.

It will be appreciated that if the modified neurotoxin is potent, it will block the cell receptors of the test cells and prevent the Semliki Forest virus from penetrating those cells and producing viral plaques. If the test modified neurotoxin is not potent or the potency is low, substantial numbers of virus particles will penetrate the cells and produce large numbers of viral plaques. Thus, by counting the number of viral plaques which are produced in the test procedure, the relative potency of the particular test modified neurotoxin can be determined. However, it is preferred to determine the percent reduction of viral plaques in the test procedure by comparison with a control culture prepared in the same manner as the test culture, with the exception that the cells are not treated with the test modified neurotoxin. In other words, the procedure for the control culture is to prepare the thin cell sheet and then directly inoculate the cells with the Semliki Forest virus. Thereafter the procedure is conducted in the same manner as discussed above. By counting the plaques in the control culture and the plaques in the test culture, the percent reduction of plaques may be easily determined. These results are expressed as "plaque forming units" (PFU) where the number units are determined by known statistical methods, e.g. the Reed-Muench method, and are expressed as the log of the reduction of plaques on a ten-fold dilution basis (thus, a plaque reduction of 100 fold equals a 2.0 log reduction).

The accuracy of determining the number of plaques in the test culture (and/or the control culture) is significantly enhanced by providing in the culture a supravital dye, which will accomplish greater contrast between the plaques and the substrate, so that the plaques are more easily identified and counted. Any of the common supravital dyes may be used, e.g. certain vegetable dyes, trypan blue, Janus green, etc., but particularly good results are obtained with 0.1% by weight of an aqueous solution of neutral red. While a supravital dye is one which allows growth in its presence (non-inhibitory), it is preferred that the dye not contact the cells or virus during incubation, particularly during the early stages of incubation. Thus, the dye is more advantageous added near the end of the incubation. For example, with the use of an overlay, the dye may be placed on top of the overlay after the culture has been returned from the inverted spacial arrangement to the normal spacial arrangement. The amount of dye used will depend upon the particular dye being used. The amount of dye may be adjusted until the desired degree of contrast between the plaques and the substrate is achieved, all of which is within the skill of the art.

The incubation temperatures for both the treated and inoculated cells vary considerably, but it is preferred that the temperatures be between 4° C. and 40° C., and more preferably between 20° C. and 39° C. A preferred temperature is 37° C. Of course, incubation times sufficient to develop viral plaques will vary with the incubation temperature and should be accordingly adjusted. In this regard, incubation time will also vary with the initial concentration of the viral inoculant, potency of the modified neurotoxin, number of cells, stage of detoxification/atoxicity, etc. Thus, incubation times of up to 48 hours or more may be advantageously used, but if desired the incubation may be carried out for longer times, e.g., up to 72 hours.

The invention will be illustrated by the following example, where all percentages and parts are by weight, unless otherwise indicated. However, it should be understood that the invention is not limited to the example but extends to the breadth disclosed above.

EXAMPLE

Materials

Baby hamster kidney cells of the clone 13 cell line (noted as BHK-21) are provided as a monolayer in bottles by Flow Laboratories.

The maintenance medium (substrate) of the cells is mimimum Eagle maintenance-80%, fetal calf serum-10%, tryptose phosphate broth 10%, 1-glutamine 3% solution-1%, sodium bicarbonate 8.8%-concentration 1%, and gentamicin 50 mg/ml-0.5%.

The plaquing overlay medium is basic medium Eagle 2x-80%, fetal calf serum-10%, lactalbumin hydrolystate-1%, Noble or Bacto-purified agar-1.2%, sodium bicarbonate 8.8%-concentration 1%, and gentamicin 50 mg/ml-concentration 0.5%.

The Semliki Forest virus is obtained from the American Type Culture Collection, conditioned by passage through 15 mice. The virus is adapted to BHK-21 cells by serial growth thereon and produces good plaques in three passages. Stock virus pools are made from virus grown on cells with the above-noted maintenance media. Aliquots of the virus are placed as seed in flame-sealed ampules and stored at −70 C.

The plaques are revealed by the addition of 0.2 ml of neutral red solution (0.01% by weight of dye in water) to each overlaid culture.

Procedure 0.2 ml per cell sheet of modified neurotoxin (MN) is placed on the cells in an undiluted solution and the treated cells are incubated for 60 minutes at 37° C. The Semliki Forest virus is added from a tenfold dilution series with one dilution to one or more bottles of cells. The cells with MN and virus added are incubated for a further period of 60 minutes at 37° C. After incubation the cells are examined microscopically. Any significant residual venom toxicity will cause cell destruction in this test and, therefore, the test functions as an index of atoxicity. At this time the overlay is added and the cultures incubated for 48 hours with the cell sheet uppermost. The neutral red solution is added to the bottles by turning the bottles over so the cells are on the bottom side and the neutral red dye is added to the overlay. Thereafter the cells are incubated for an additional 8 hours at 37° C. The dye penetrates the overlay and effects the stains at this time.

Results

The number of plaques in the cell sheet pretreated with modified neurotoxin before infection with the virus is compared with a virus control prepared in the same manner as the test cultures, but where the cells received no prior treatment with MN. A plaque reduction of 50% which is a 0.3 log reduction of plaque forming units (PFU) is considered significant. The log values of the PFU in the pretreated cells and the virus control are shown in Table 1.

Table 1.

Ability of Various Lots of Modified Neurotoxin to Inhibit Infection of BHK-21 Cells by Semliki Forest Virus

| Lot of MN | Log PFU Virus Control | Log PFU MN Treated Cells | Log PFU Inhibition |
| --- | --- | --- | --- |
| A | 8.8 | 6.0 | 2.8 |
| B | 8.8 | 6.0 | 2.8 |
| C | 8.7 | 5.4 | 3.3 |
| D | 7.6 | 5.3 | 2.3 |
| E | 8.2 | 6.4 | 1.8 |
| F | 8.3 | 6.4 | 1.9 |
| G | 8.9 | 7.0 | 1.9 |
| H | 8.9 | 7.0 | 1.9 |

As can be seen from the table, the controls varied from Log PFU 8.9 to 7.6, but primarily between 8.2 and 7.6. Lot A of the MN showed a log PFU inhibition of 2.8 (50% plaque reduction is approximately equal to 0.3 log) which demonstrates very high potency. Lot B was identical to A.

Lot C of the MN, however showed an exceptionally high potency, i.e. log PFU of 3.3 while Lot D showed a log PFU of 2.3, which is still quite high.

However, Lot E showed a log PFU of 1.8 and Lots F, G and H showed 1.9. These latter Lots still exhibit quite satisfactory inhibition, but it can be seen that the potency of the MN may vary at least one log.

Each of the Lots demonstrated atoxicity by microscopic examination.

Also, from the above table, the importance of the present invention can be easily appreciated. Simply stated, the potency achieved in detoxifying various lots of snake venom to produce the MN can vary considerably. This simply reflects the fact that venom harvested from different snakes at different periods and at different maturities can have different toxic potency, which, in turn, yields different potencies of the MN. In addition, the handling of the venom after harvesting and prior to detoxifying to produce the MN can effect the potency of the resulting MN. While these variables still, usually, produce an MN within acceptable administration, it would be of substantial benefit to provide a convenient test for establishing the potency of a particular lot of MN, and, thus, allow the adjustment of the dosage of the MN to achieve a relative level administration of effective ingredients. Before the present invention, no convenient test of that nature was available and potency could not be conveniently proved. With the present invention, however, a more uniform administration of the effective ingredients is now possible, which in turn, allows a more ordered treatment with the modified neurotoxin.

In addition, the test provides an easy means for determining toxicity/atoxicity and the test can be carried out rapidly enough that it forms a valuable tool in following the detoxification process. This allows stopping the detoxification process at the optimum end point, after atoxicity is achieved, but before deterioration of the potency commences.

Finally, this test provides a very valuable tool in subsequently proving the potency and atoxicity of any particular lot of modified neurotoxin which may be suspected of either losing potency or having developed toxicity, because of unusual storage, handling or transit conditions.

Under the above circumstances, the invention provides a very important advantage to the art.

What is claimed is:

1. A test method for determining the absence or presence of toxins in and the potency of modified neurotoxins comprising:
   (a) providing on a growth substrate a thin sheet of viable cells which exhibit an uninhibited growth potential of at least $10^6$ Plaque Forming Units of Semliki Forest Virus under the test conditions, the cells being harvested from the kidney cells of an embryo, fetus or baby specimen of a fowl or animal,
   (b) treating the thin cell sheet with test modified neurotoxin and incubating the treated cell sheet for at least ½ hour;
   (c) examing the incubated cell sheet for cell destruction, wherein the absence of cell destruction shows the absence of toxins in the modified neurotoxin and the presence of cell destruction shows the presence of toxins in the modified neurotoxin;
   (d) inoculating the treated cell sheet with Semliki Forest Virus; and
   (e) counting the number of viral plaques in the remaining culture, whereby the potency of the modified neurotoxin is determined by the percent reduction in viral plaques produced by the use of the modified neurotoxin in the culture.

2. The method of claim 1 wherein the percent reduction of viral plaques is determined by comparison with a control culture which is identical to the test culture except that the cells are not treated with the modified neurotoxin.

3. The method of claim 1 wherein the examination is a microscopic examination.

4. The method of claim 1 wherein the animal is baby hamster.

5. The method of claim 1 wherein the thin cell sheet has no more than 3 layers of cells.

6. The method of claim 5 wherein the thin cell sheet has no more than 2 layers of cells.

7. The method of claim 5 wherein the thin cell sheet is a monolayer of cells.

8. The method of claim 1 wherein the treated cells are incubated at temperatures between 4° C. and 40° C.

9. The method of claim 1 wherein the inoculated cells are incubated for at least 1 hour at temperatures between 4° C. and 40° C.

10. The method of claim 9 wherein the inoculated cells are overlaid with a solid inert growth or maintenance overlay medium either prior to or during incubation of the inoculated cells.

11. The method of claim 10 wherein the overlay is placed on the cells after the inoculated cells have been incubated for at least 1 hour.

12. The method of claim 10 wherein the culture of overlaid cells is inverted during at least a part of the incubation period so that the cells are uppermost in the culture.

13. The method of claim 10 wherein a supravital dye is added to the overlay to increase the contrast between the plaques so that the plaques are more easily identified and counted.

14. The method of claim 1 wherein the Semliki Forest virus is conditioned to the cells by passage through the cells prior to use in the test procedure.

15. The method of claim 1 wherein the virulence of the Semliki Forest virus is increased by multiple passage through animals.

16. The method of claim 15 wherein at least 3 passages are used.

* * * * *